United States Patent [19]

Ehrenfeld

[11] Patent Number: 5,116,614
[45] Date of Patent: May 26, 1992

[54] JOMOL DERIVATIVES AS AGENTS FOR THE USE IN MALIGNANT TUMORS AND LOWERED IMMUNE DEFENSES

[76] Inventor: Udo Ehrenfeld, Furtmayrstr. 20, 8400 Regensburg, Fed. Rep. of Germany

[21] Appl. No.: 468,269

[22] Filed: Jan. 22, 1990

Related U.S. Application Data

[62] Division of Ser. No. 842,313, Mar. 21, 1986.

[30] Foreign Application Priority Data

Mar. 25, 1985 [DE] Fed. Rep. of Germany ....... 3510795

[51] Int. Cl.$^5$ .................... A61K 39/02; C12N 1/20
[52] U.S. Cl. .................... 424/92; 424/1.1; 435/253.2; 514/2; 530/402; 530/403
[58] Field of Search .............. 424/1.1, 92; 534/14; 435/253.2; 514/2; 530/402, 403

[56] References Cited

U.S. PATENT DOCUMENTS 4,590,060 5/1986 Ehrenfeld ..................... 424/1.1

OTHER PUBLICATIONS

J. Drews (1984): "Immunostimulation, Clinical and Experimental Perspectives" in Klin. Wochenschr. (1984) 62, 254–264.

R. Barot-Ciobaru et al. (1981): "Antitumor activity of intralesionally administered Nocardia opaca preparations in rat and mouse tumors: A comparison with BCG and Corynebacterium parvum" Int. J. Immunopharmac. vol. 3, pp. 115-122 (1981).

C. H. J. Ford and A. G. Casson (1986): Antibody mediated targeting in the treatment and diagnosis of cancer: an overview Cancer Chemother. Pharmacol (1986) 17; 197–208.

G. Poste et al. (1982): "Analysis of the fate of systemically administered liposomes and implications for their use in drug delivery". Cancer Research 42, 1412-1422 (1982).

Primary Examiner—John S. Maples
Attorney, Agent, or Firm—Ostrolenk, Faber, Gerb & Soffen

[57] ABSTRACT

The invention relates to Jomol, processes for its production of Nocardia opaca cells (DSM 43202 or ATCC 21953, respectively), its derivatives, diagnostic compositions, and pharmaceutical preparations containing Jomol or its derivatives, as well as to products containing Jomol and/or one of its derivatives and an adjuvant.

8 Claims, 4 Drawing Sheets

UV spectrum of the crude preparation G2 of Nocardia opaca before fractioning in Sephadex G75

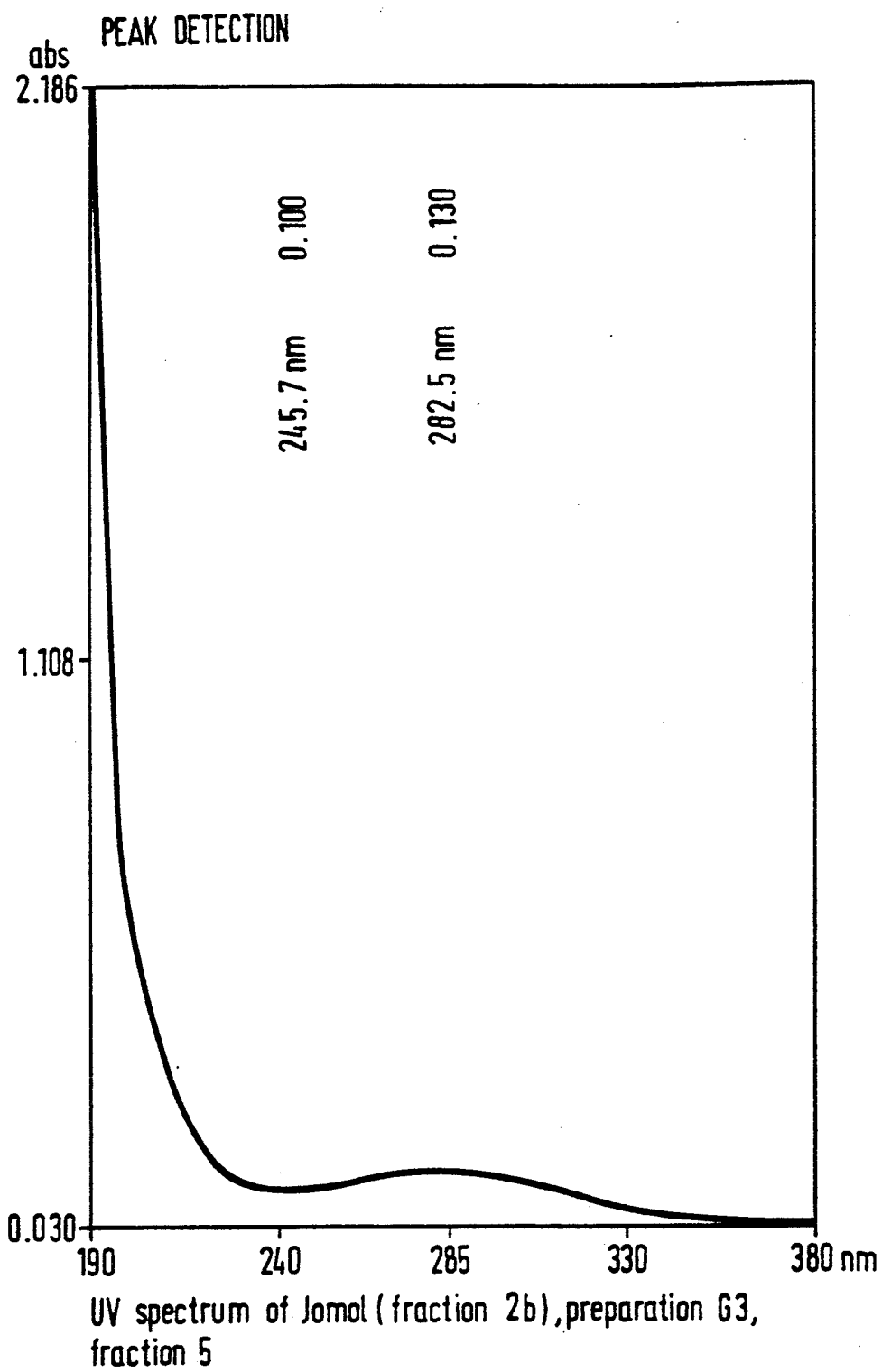

gel chromatography of Jomol at Sephadex G75;
eluent: 0.01 M tris-HCl ph 7.4, 0.06% EDTA-Na Human Serum Albumin and Vit. $B_{12}$ chromatographed under the same conditions as Jomol (in Fig. 3a)

FPLC-chromatogram for characterizing the Jomol-DTPA −$^{111}$In

JOMOL DERIVATIVES AS AGENTS FOR THE USE IN MALIGNANT TUMORS AND LOWERED IMMUNE DEFENSES

This is a division of application Ser. No. 06/842,313, filed Mar. 21, 1986.

This invention relates to Jomol, Jomol derivatives, processes for the production of these compounds, their use and products containing Jomol or Jomol derivatives.

Jomol and its derivatives can be used as pharmaceutical preparations and diagnostic compositions. They are especially suited as agents for increasing the cellular defense and for the diagnosis and treatment of malignant tumors as well as for the treatment of weaknesses of the cellular and humoral immune defenses. Jomol can be used as a carrier for diagnostic and therapeutic substances.

The diagnosis and treatment of malignant tumors is still difficult today despite intensive research. It is practically impossible to recognize malignant tumors at an early stage and up to now there has been no method available by which an early diagnosis can be effected. The treatment of malignant tumors is—as is commonly known—not satisfactory.

U. Ehrenfeld (Krebsgeschehen 5, 132 et seq. (1979)) reports on the cancerotoxic effect of a mixture of acetaldehyde and ethanol. The mixture contains 3 to 10 g of acetaldehyde per 1000 g of ethanol. It has been found, however, that the action of this mixture is not sufficient for the treatment of solid malignant tumors or of metastases.

In the German laid open prints DE-OS 3 334 751, DE-OS 3 336 583 and DE-OS 3 402 312 (corresponding to the European patent application 84 110 118, the Japanese patent application 202 859-84 and the U.S. patent application Ser. No. 689,728 (date of filing: Jan. 4, 1985) and 557,738 (date of filing: Dec. 2, 1983)) an agent for the diagnosis and treatment of malignant tumors as well as for the treatment of weaknesses of the cellular and humoral immune defenses are described, which contains an immunomodulator in and/or on liposomes or lipidized, or an immunomodulator tagged with a radioactive tracer, a dyestuff or a cytostatic. Such an immunomodulator is preferably administered together with an agent containing an aldehyde of formula RCHO, in which R is a hydrogen atom or a straight-chain or branched hydrocarbon group having 1 to 4 carbon atoms, and optionally an alcohol of formula $R^1CH_2OH$, in which $R^1$ has the meaning indicated above for R. The agents described above in the German laid open prints are highly effective and suited especially for the treatment and diagnosis of malignant tumors.

However, there is a need for agents which show possibly no side-effects and can easily be produced. The known agents have the disadvantage that the intravenous administration thereof is combined with certain difficulties in some modifications.

It is the object of this invention to provide an agent and a product for the diagnosis and treatment of tumors, by which lowered immune defenses in man and animal can also be successfully treated. The agent is to be highly effective so that it can therefore be administered in lower concentrations than the known agents. It is to be of unlimited availability, simple to use and it is to be easily dosed. The agent of the invention is to result in less severe stress on the patient's organism. In addition, the agent is to be administrable intravenously and serve as carrier for radioactive tracers, pharmaceutical preparations and dyestuffs.

It has surprisingly been found that a compound obtained from the microorganism Rhodococcus rhodochrous solves the object according to the invention.

The invention relates to Jomol characterized by the following properties:

(1) absorption maximum in the UV spectrum at 282.5 nm;
(2) apparent molecular weights at 4500, 3000 and 900;
(3) high degree of hygroscopicity;
(4) depending on the residual water content, of ivory color amorphous-crystalline-flaky;
(5) pH value of 5.5 (1 mg of the compound, dissolved in 1 ml of water);
(6) slightly positive, pink ninhydrin reaction;
(7) stainable with orcine reagent;
(8) peptide portion: about 50%, based on the amorphous substance (protein test MicroBioRad according to L. Thomas, J. Clin. Chem. Clin. Biochem., Vol. 19, 1981, pages 203 to 208, company: BioRad, Munich; Coomassie Brilliant Blue G 250 ®);
(9) the following $R_f$ values (solvent indication volume:-volume)
 $R_f=0.20$ (butanol:glacial acetic acid:water 4:1:1)
 $R_f=0.45$ (benzene:glacial acetic acid:water 2:1:2)
 $R_f=0.685$ (methanol:glacial acetic acid:water 4:1:1)
 no migration (chloroform:methanol 96:4)
 $R_f=0.54$ (chloroform:methanol 1:1);
(10) solubility: poor solubility in non-polar solvents, very good solubility in polar solvents;
(11) identifyable constituents:

| substances | ratio (approach) |
|---|---|
| neutral sugars (glucose, galactose, ribose) | $(\leq)1$ |
| amino sugars (glucosamine, muramic acid) (after hydrolysis) | 3.5 |
| amino acids (ala, glu, iso-gln, gly, lys, DAP) | 4 |
| lipids | <1 |
| phosphorus | <1 |

(12) structure:
 peptidoglycan structure, the glycan skeleton of which consists of 10 to 80 disaccharides of N-acetylglucosaminyl-N-acetylmuramyl,
 the following applying:

| ala | alanine |
|---|---|
| glu | glutamic acid |
| gly | glycine |
| iso-gln | iso-glutamine |
| lys | lysine |
| DAP | meso-α,ε-diaminopimelic acid |

Furthermore, the invention relates to a process for the production of Jomol by culturing a strain of Nocardia opaca cells and collecting the cells from the culture. The process according to the invention is characterized in that (a) Nocardia opaca cells (DSM 43 202 or ATCC 21953, respectively) are cultured on a buffered culture medium,
(b) the cells are collected, (c) the cells are suspended in a medium containing glucose and buffer, the suspension is set aside for 15 minutes to several hours, (d) the suspension is treated in a buffer with a murolytic enzyme, preferably with lysozyme, and optionally with deoxyribonuclease, (e) the cells are destroyed, (f) the resulting material is separated into sediment and supernatant, (g) the supernatant is subjected to separation on Sephadex columns by using a buffer as eluent, which can optionally contain 0.1 to 0.05% EDTA-Na$_2$, (h) the active fraction is obtained, and (i) the active fraction is reacted with acetaldehyde, whereby the buffer used can be potassium phosphate buffer, tris-HCl buffer (tris hydroxy methyl amino methane HCl buffer), ammonium acetate buffer and others.

Furthermore, the invention relates to a pharmaceutically acceptable Jomol derivative, characterized in that it contains the above-described Jomol and coupled therewith a crown ether, diethylenetriamine pentaacetic acid, uridine, L-thyronine, L-tyrosine, fluorescein isothiocyanate or tin-(II)-chloride.

Moreover, the invention relates to tagged Jomol or a tagged Jomol derivative, characterized in that it contains the above-described Jomol or one of its pharmaceutically acceptable derivatives, as mentioned above, tagged with $^{99m}$technetium, $^{111}$indium, $^{123}$iodine, $^{125}$iodine, $^{130}$iodine, $^{131}$iodine, $^{132}$iodine or $^{224}$radium, a dyestuff or cytostatic. The coupling agents used can be all coupling agents which can carry or bind a radioactive tracer, a dyestuff or a cytostatic.

Furthermore, the invention relates to Jomol, as described above, a pharmaceutically acceptable Jomol derivative, as described above, tagged Jomol or a tagged Jomol derivative, as described above, in and/or on liposomes or lipidized.

Moreover, the invention relates to a diagnostic composition containing Jomol or a Jomol derivative, as described above, tagged with a radio-isotope and/or a dyestuff, as well as optionally conventional carriers and/or diluents, and a pharmaceutical preparation containing Jomol or a Jomol derivative, tagged with a dyestuff, a cytostatic or a radio-isotope, and optionally conventional carriers and/or diluents.

Finally, the invention relates to a product containing (1) a diagnostic composition or a pharmaceutical preparation, as described above, and (2) an adjuvant containing an aldehyde of formula I

RCHO              (I)

in which R is a hydrogen atom and a straight-chain or branched hydrocarbon group having 1 to 4 carbon atoms, in which connection the free aldehyde may also be metabolically liberated directly or indirectly by substances, and optionally an alcohol of formula II

R$^1$CH$_2$OH            (II)

in which R$^1$ has the meaning indicated above for R, and optionally conventional pharmaceutically acceptable excipients and/or diluents for the simultaneous, separate or stepwise application in time upon the diagnosis and treatment of malignant tumors and for the treatment of lowered immune defenses.

BRIEF DESCRIPTION OF THE DRAWINGS

FIG. 2 is a UV spectrum of JOMOL (fraction 2b), preparation G3, fraction 5;

FIG. 3b shows human serum albumin and Vitamin B$_{12}$ chromographed under the same conditions as JOMOL in FIG. 3a; and FIG. 4 is an FPLC chromogram for characterizing JOMO-DTPA-$^{111}$In.

Figure 1:
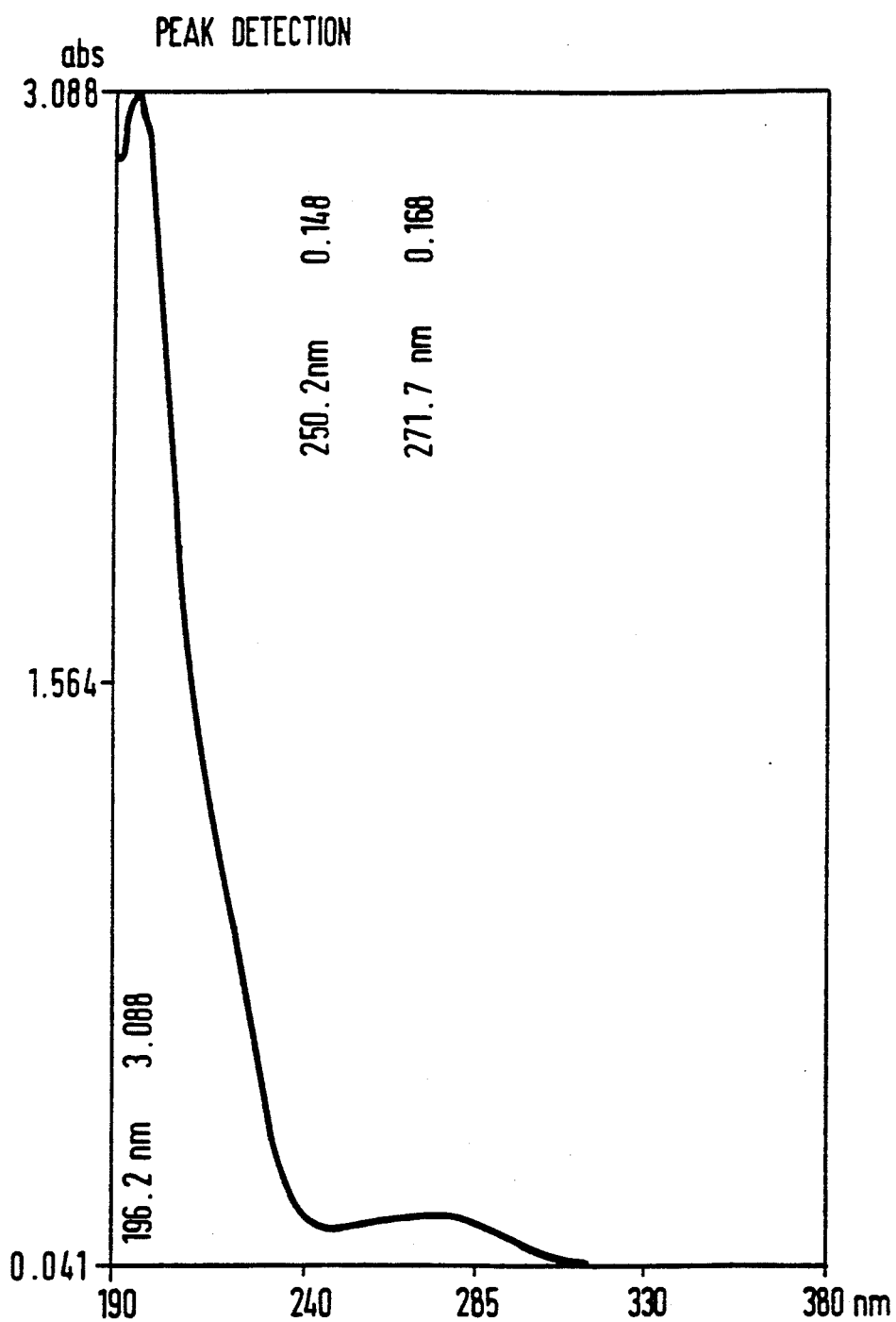
FIG. 1 is a UV spectrum of the crude preparation G2 of Nocardia opaca before fractioning in Sephadex G 75.

The applicant has surprisingly found that a certain microorganism of the genus Nocardia opaca, i.e. Rhodococcus rhodochrous, forms a compound which, after reaction with acetaldehyde, has surprising properties as an agent for increasing the cellular immune defense and as a carrier for diagnostic and therapeutic substances. The strain Rhodococcus rhodochrous was deposited by the Deutsche Sammlung von Mikroorganismen (German Collection of Micro-Organisms), Griesbachstrasse 8, 3400 Göttingen, Federal Republic of Germany, on May 16, 1972; No.: DSM 43 202 (=DSM 363=ATCC 21 953). The strain is freely available, and its viability was shown again on Feb. 28, 1985.

When carrying out the process according to the invention, a culture medium containing a carbon source, a nitrogen source and minerals is used. This culture medium can also contain antifoam agents and/or other conventional components. Examples of carbon sources are carbohydrates, alcohols, hydrocarbons and bran. Examples of nitrogen sources are Indian corn spring water, yeast extracts, beef extracts, peptones, fish-meal, ammonium salts, nitrate salts and urea. The mineral source comprises inorganic salts, such as phosphates, magnesium salts, zinc salts, calcium salts, manganese salts, molybdenum salts and copper salts.

The composition of the culture medium may be varied as required, and, during fermentation, these carbon, nitrogen and mineral sources can be additionally added. For producing an inoculum, the micro-organism is cultured, e.g., on DST-Oxoid (culture medium, company: Oxoid, Wesel, Federal Republic of Germany) or glucose agar (2%) in plate technique on three to four plates for five to eight days. As a result, a product is obtained, which can then be used as an inoculum for the production of the material in a commercial scale.

Culturing the micro-organism on a commercial scale may, for example, be effected in Erlenmeyer flasks containing 100 ml of ordinary nutrient broth. Culturing takes place under aerobic conditions.

The culturing temperature is between 20° and 40° C., and the pH value of the culture medium is at 7.2 to 7.4. The preferred temperature is 30° to 37° C., and the suitable culturing period is usually 2 to about 30 days and can be varied in a suitable way, depending on the selection of the other culture conditions.

Then, the bacteria are collected, preferably by centrifugation. However, the bacteria can also be filtered off by glass filters. Centrifugation can be effected, e.g., with 4000 rpm in a Roto-Silenta-K-Hettich cooling centrifuge with a rotor of 40 cm in diameter for a period of 5 to 10 minutes. The resulting bacteria are usually washed, e.g. with water or a buffer, such as, for example, 0.01M (molar) tris-HCl buffer having a pH value of, e.g., 7.4. The tris-HCl buffer contains preferably EDTA-$Na_2$, for example 0.1 to 0.04, preferably 0.06%. The washing step can be repeated once or several times. Examples of other usable buffers are potassium phosphate buffer or ammonium acetate buffer. It is a special advantage of the process according to the invention that the same buffer may be used throughout, i.e. in all steps.

Then, preferably after they have been washed as above, the bacteria are suspended in tris-HCl buffer (pH 7.4), e.g. 0.01M, containing preferably 0.1 to 0.05% EDTA-$Na_2$ and 8 to 12%, preferably 10%, glucose, or in one of the other buffers indicated above.

Then, a murolytic enzyme, preferably lysozyme (Lysozyme, Sigma L-6876 ®, Sigma, Munich, Federal Republic of Germany), is added to the resulting suspension which was optionally incubated, and preferably to remove the nucleic acids and to reduce the viscosity deoxyribonuclease is added (Deoxyribonuclease, Sigma D-0876 ®). For example, for 5 g of bacteria 100 ml of tris-HCl buffer are used and then, 10 mg of lysozyme and 3 mg of deoxyribonuclease are added to this suspension.

The treatment with glucose and the ferments is carried out at a temperature of 20° to 40° C., preferably 30° to 37° C., for a period of 30 minutes to several hours, preferably for a period of two to three hours.

The reaction mixture is then set aside for a period of 10 minutes to several hours.

Alternatively, the reaction mixture can also be incubated at a temperature of 30° to 37° C. for a period of 10 minutes to several hours, preferably 20 hours. If incubation is carried out, a separation into sediment and supernatant will then follow. Such a separation is effected, for example, by centrifugation. The sediment is then again resuspended in tris-HCl buffer (pH 7.0, preferable 0.01 molar) containing preferably 0.06% EDTA-$Na_2$ or in one of the other above-mentioned buffers. Optionally it can be washed with this buffer once or several times. The washing step may be omitted, however, it serves to remove more bacterial wall material from the concludingly used supernatant.

Then, the cells are destroyed. This can be done by all suitable methods, e.g. by ultrasonication. It is preferred to apply ultrasonication for, e.g., one minute, for example with the "Sonicator cell disruptor" from Kontron Ultrasonics, type W 185 F ®, 15 mm end range, step 3, scale at 50. The mechanical destruction of the cells does not have to be carried out, however it is perferably carried out because the yield of the desired product is thus increased.

The resulting material is then separated into supernatant and sediment, preferably by centrifugation. Centrifugation can be carried out in an ordinary centrifuge, however, it is carried out preferably in a cooling centrifuge at a temperature of 4° to 6° C. at 4000 rpm for 10 to 15 minutes. The sediment can optionally be washed with water or one of the above-mentioned buffers once or several times, the resulting washing solutions being united with the supernatant. Optionally after concentration in high-vacuum at low temperatures, the supernatant is chromatographed on Sephadex-G-75 columns. If washing of the resulting sediment is omitted, the supernatant will be subjected directly to chromatography, being concentrated.

5 g of bacteria, e.g., yield a supernatant which is preferably separated into five equal portions and then each of five prepared Sephadex-G-75 columns is supplied with one portion thereof. The columns have a length of 80 cm, the inner diameter is 2.5 cm, and the Sephadex filling height is 60 cm. If only one column is used, the portion which is not chromatographed will be frozen at −25° C. and stored at this temperature.

Figure 3A:
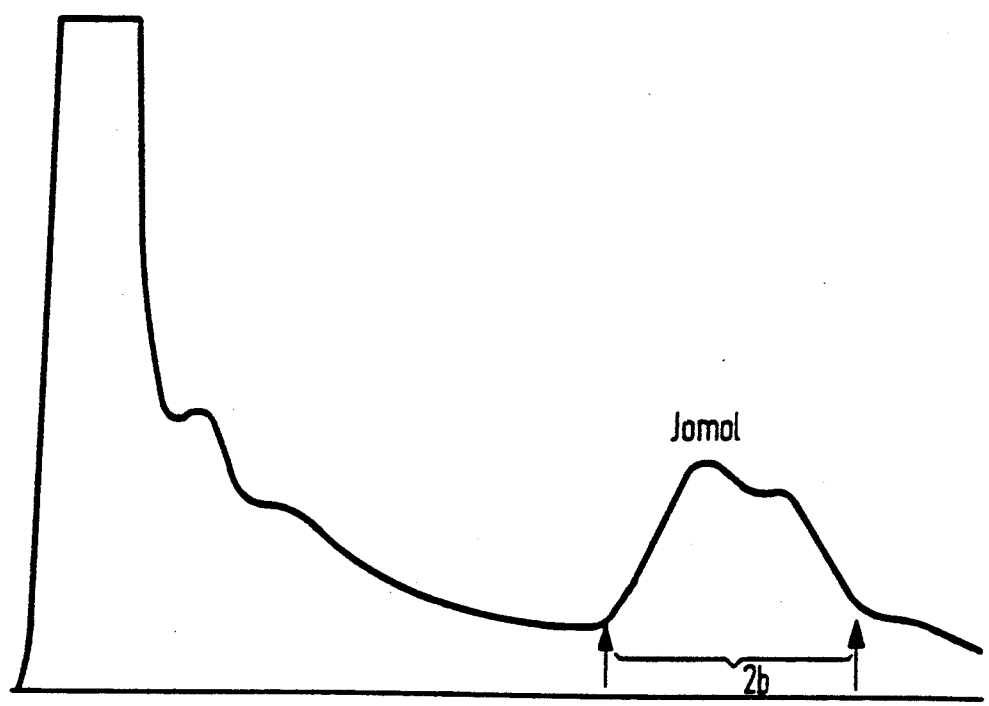
FIG. 3a is a gel chromagraph of Jomol in Sephadex G 75; eluent: 0.01M Tris-HCl pH 7.4, 0.06% EDTA-Na.
Figure 3B:
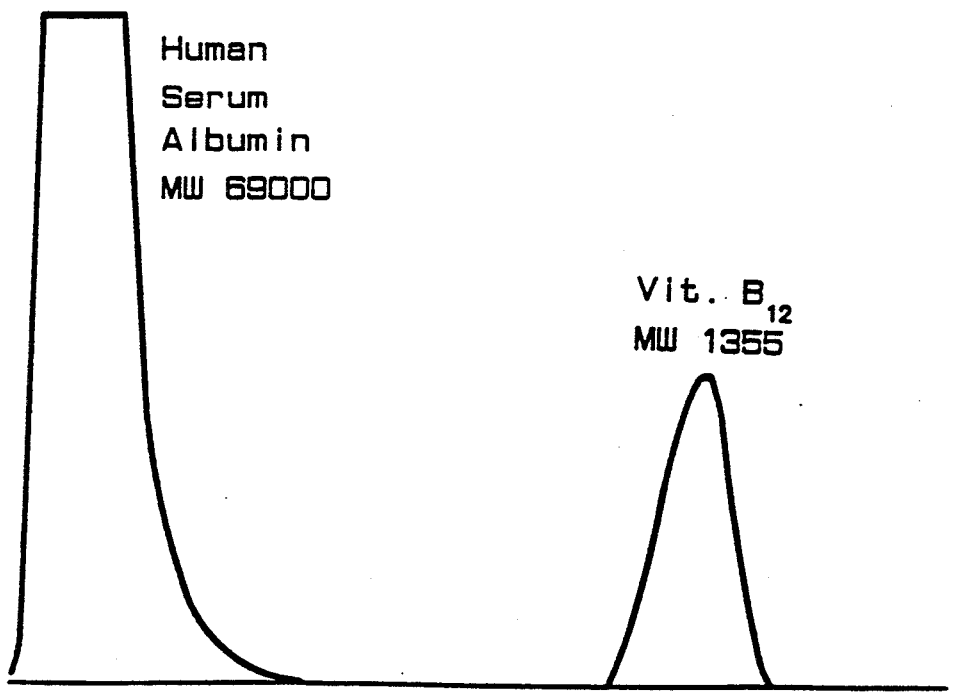

If during chromatography in one of the columns "Albumin aus Humanserum Markierung" (albumin of human serum labeling) (order number 11885, Serva, Heidelberg, Federal Republic of Germany) is used for analyzing the substance, the first peak of the crude substance flows out with the albumin (MW 69 000) and the fraction 2b* flows out with the vitamin $B_{12}$ (MW 1 355,4) also used for column calibration (see FIG. 3b).

The eluent used is 0.01M tris-HCl buffer (pH 7.4) containing 0.06% EDTA-$Na_2$. The rate of elution is 100 $\mu l$ per minute, lower or higher rates being also applicable. The active fraction which is termed fraction 2b* is collected in a period of 12 to 14 hours after the beginning of gel chromatography. The elution volume is about 900 to 980 ml, the fractionation is carried out using UV detection at 214 nm (see FIG. 3a). For obtaining the fraction 2b*, the steps from collecting the cells after cultivation to column fractionation can also be carried out in phosphate buffers, ammonium acetate buffers and others. The use of ammonium acetate buffer is especially preferred for the preparations for iodination.

The resulting active fractions are lyophilised and then incubated at 80° C. for one hour to destroy the proteases. If lyophilisation does not take place, the dilute solutions are frozen at −20° C., preferably at −40° C., very preferably at −80° C. and stored as a solution. Prior to lyophilisation and/or freezing, the resulting solutions of the active fractions are mixed with a 1M acetaldehyde (extremely pure) aqueous solution in the molar ratio given hereinafter and set aside at room temperature for 10 minutes to 2 hours, preferably, for example, for 30 minutes.

It was surprisingly found that a "fraction 2b" is obtained when reacting the active fraction 2b* with acetaldehyde. This fraction 2b is termed Jomol and has surprising pharmacological properties and can also be used as a carrier.

The fraction 2b* is reacted with acetaldehyde in a molar ratio of fraction 2b*:acetaldehyde=1:1.8 to 2, preferably in a ratio of 1:2, a mean molecular weight of about 4000 being assumed for the fraction 2b*. As explained above, Nocardia bacteria are used in the process according to the invention. Nocardias are gram-positive bacteria. Their multilayered cellular wall basic skeleton has inclusions of proteins and polysaccharides. Applied thereon are coating layers which can hardly be removed.

The outer layer of the bacterial wall contains lipoproteins (and, among other compounds, waxes), the intermediate layer contains lipopolysaccharides and the inner layer contains polysaccharide chains (murein skeleton). The antigenicity of the layer constituents decreases from outside to inside.

The substrate for the production of Jomol is the inner layer with the long peptidoglycan chains. They are formed of disaccharide blocks in the glycan skeleton. The disaccharide block consists of N-acetylglucosaminyl-N-acetylmuramyl:

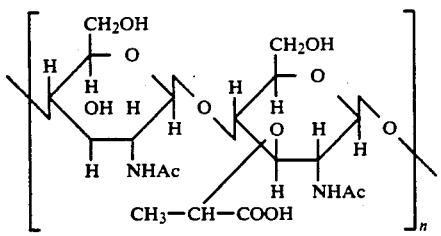

Peptide units are bound via L-alanine to the acid group of N-acetylmuramic acid (N-acetylglucosamine lactate ether). These peptide units can contain sequences of L-alanine-D-isoglutamine-meso-$\alpha,\epsilon$-diaminopimelic acid (DAP), whereby the DAP can be amidized. In its place, uridine diphosphate or another amino acid occurs in rare case, L-lysine is more common, which in turn may be substituted. Instead of the acetyl group, a glycolyl group may be present at the muramic acid. In addition to these units mentioned, there may also be present 0 to 10% neutral sugars.

In the above production process, the portion of the outer wall layer of the Nocardia bacteria will be discarded. Peptidoglycans with lipids and waxes are thus contained in neither the total preparation nor the preparation fraction 2b. The produced preparations are cleavage products of peptidoglycans of the inner wall layer. The lysozyme used for cleavage hydrolyses the bond between N-acetylglucosamine and N-acetylmuramic acid of the glycan skeleton. The deoxyribonuclease decreases the viscosity of the product. The interpeptide bonds of the peptide substituents of the peptidoglycans are partially split so that they become water-soluble and are fat-soluble only to a minor extent. At the same time, the ends of the peptidoglycan chains lose their peptide portions. Due to the production process, the peptidoglycans become free of natural lipids to a maximum extent, together with which they are present in the bacterial walls. The N-acetylglucosamine groups of the peptidoglycans may be partially desacetylated.

About 5 g of bacteria yield about 2 mg of Jomol in pure condition.

The product is very hygroscopic. Weighing under access of humidity (air) does not permit exact indications of substance amounts; therefore, weighing takes places in the previously weighed closed vessel after lyophilisation. Optionally, the water content of the lyophilisate can be determined by conventional methods.

After drying, the substance is of yellowish white color and flaky, with some water it appears "crystalline" at the moment; with some more water it is colorless, glass-like, gelatinous and forms filaments just like household all-purpose glues do. In sterile storage without access of light under nitrogen, the substance is stable at a temperature below $-25°$ C. Under access of light the substance is stable at room temperature for several hours.

Jomol is volatile, except in solutions at 0° C. In the freeze-dried state this behavior of the substance was not observed. If, for example, Jomol or a product containing it is kept in an aqueous solution in a plastic vessel at room temperature for five days, a loss of about 50% of the substance will be observed. The effect does not occur in frozen medium.

Jomol has unexpected properties. Jomol itself is used as an immune modulator, pharmaceutical preparation or diagnostic. Jomol and its coupling products with certain coupling agents are especially suited as carriers for radioactive compounds, dyestuffs and pharmaceutical agents, preferably cytostatics.

Jomol, its coupling products and the tagged or charged Jomol derivatives surprisingly accumulate on cancer cells and are hardly bound by healthy cells or bound only to a minor extent. It is assumed that it is bound to cleavage sites in the cancer cell wall matrix which are formed by endogeneous protease. If, for example, Jomol is tagged with a radioactive marker and administered, the tagged Jomol will accumulate on the tumor cells and, due to this, the latter can be easily detected by means of gamma-camera imaging.

Examples of coupling products of Jomol are products containing Jomol, coupled therewith a crown ether, diethylenetriamine pentaacetic acid, uridine, L-thyronine, L-tyrosine, fluorescein isothiocyanate or tin-(II)-chloride. Such coupling products are generally produced by dissolving Jomol in a suitable polar solvent or in an aqueous solution of a polar solvent. For example, 1 to 10 mg of Jomol can be dissolved in 5 to 200 $\mu$l of a suitable aqueous solvent. Highly concentrated solutions of Jomol can also be prepared. Dissolving takes place at a temperature as low as possible, whereby, however, the temperature has to be such that the solvent does not yet crystallize. The substance to be reacted with Jomol is reacted in a ratio of 1 mol Jomol to 0.8 to 1.2 mol of the compound to be coupled, a mean molecular weight of about 4000 being assumed for the Jomol. The compound which is coupled to Jomol is dissolved or homogeneously suspended in an anhydrous medium. In the case of tin-(II)-chloride, a hydrochloric aqueous solution is used.

The reaction mixture is set aside at a temperature in the range of 15° to 40° C. for a period of several minutes to 60 minutes. The product can be used directly. It can also be purified and isolated by chromatography.

Chromatography and purification are effected in a similar way as is described for Jomol itself. Sephadex columns are used, and the above-mentioned buffers are used as eluents.

The active fractions collected are fractions flowing out in ml 5 to 10 from a 25 cm long, diameter: 0.6 cm, column, Sephadex G 75 filling height: 15 cm, uniform eluent layer on top 8 cm above Sephadex height, previously equilibrated with the desired fractions, or corresponding to the first two peaks of Jomol in UV detection at 214 nm.

If the coupling products themselves are used directly as a diagnostic or pharmaceutical preparation, it is preferred to react solutions as pure as possible and to use the resulting solutions directly as pharmaceutical preparations, optionally after sterilisation.

The following coupling products were produced:

1. Coupling product of Jomol and diethylenetriamine pentaacetic acid anhydride

This product is termed "Jomol-DTPA" or "Jomo-In". It is suited for charge with $^{111}$indium or with $^{99m}$technetium, which was reduced with tin-(II)-chloride.

The products tagged with a radioactive marker are especially suited for diagnosis.

2. Coupling product of Jomol and tin-(II)-chloride

This product is termed "Jomol-Sn" or "Jomo-tech". Jomol-Sn is especially suited for charge with $^{99m}$technetium.

The tagged product is suited especially well for the diagnosis of tumors.

The product is produced by reacting a Jomol solution with a hydrochloric aqueous tin-(II)-solution.

3. Coupling product of Jomol and uridine

This product is termed "Jomo-J/U" and is especially suited for tagging with radioactive iodine. The tagged product can be used for diagnosis or treatment.

The production is effected by reacting Jomol and uridine-2′,3′-dialdehyde in an anhydrous solvent.

4. Coupling product of Jomol and L-thyronine

The product is termed "Jomo-J/Tn" and produced by reacting Jomol with α-amino-β-[p-hydroxyphenyl-(p-hydroxyphenylether)]-propionaldehyde.

5. Coupling product of Jomol and L-tyrosine

The product is termed "Jomo-J/TS" and is produced by reacting Jomol with α-amino-β-[p-hydroxyphenyl]-propionaldehyde.

6. Coupling product of Jomol and fluorescein isothiocyanate

The product is termed "Jomo-Color". It is especially suited for diagnosis and/or for therapeutical treatment.

The products 4, 5 and 6 are suited especially well for tagging with radioactive iodine. The products are used for diagnosis and for therapeutical treatment.

7. Coupling product of Jomol and a precursor of Kryptofix 222

This product is termed "Jomo-CE" and also "Jomo-Ra". The product is produced by reacting Jomol with a precursor of Kryptofix 222 ®, obtainable from Merck, Darmstadt, Federal Republic of Germany and termed CE. The CE molecule has the following structure:

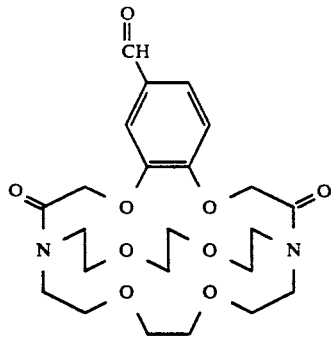

CE contains the complete amide bond in the crown ether (in contrast to Kryptofix 222).

The compound is suited especially for the radioactive tagging with radium. A longer incubation period with $^{224}$Ra for uptake is necessary than in the case of Kryptofix 222. The stability constant regarding the radium bond is the same for CE and Kryptofix 222: 1 g K = 6.64 (this logarithm is higher for radium than for all other relevant metal ions. Regarding its bond, the bound radium can only be removed by an acid environment (instable in the stomach, stable in the rest of the body).

Acidifications will have to be avoided after binding the radium to CE.

The tagged compound is suited for treatment.

Jomol and its above-described coupling derivatives are used as excipients for dyestuffs, pharmaceutical preparations, preferably cytostatics, and radioactive markers. Since, as mentioned above, these substances accumulate on cancer cells, it is thus possible to detect or treat the cancer cells as specific targets. Due to this, it is possible to apply the substances calculatedly to the cancer cells, such as, for example, the radioactive markers which, on the one hand, serve for detecting the cancer cells and, on the other hand, serve for destroying the cancer cells.

The pharmaceutical preparations used are preferably cytostatics and metastasis inhibitors. Examples of cytostatics and metastasis inhibitors which can be used according to the invention, are all compounds presently known as cytostatics and metastasis inhibitors. Examples thereof are melphalan, carmustin, lomustin, cyclophosphamide, estramustine phosphate, ifosfamide, chlorambucil, methotrexate, pegafur, fluorouracil as well as antibiotics which are used for these purposes. Examples of dyestuffs are fluorescence dyestuffs, acridine dyestuffs, such as actinomycine, and rubicine. These compounds are used for therapy and diagnosis.

The above-mentioned coupling product of Jomol and fluorescein is an especially preferred product of the invention, since it is suitable for both the diagnosis and treatment and tagging with radioactive iodine as well.

The production of tagged Jomol or the tagged Jomol derivatives tagged with a pharmaceutical preparation or a dyestuff is effected by reacting a Jomol solution as indicated above for the production of the coupling products or by reacting a solution or suspension of the coupling products in suitable concentration with a solution or suspension of a pharmaceutical preparation or a dyestuff. In general, equimolar amounts of Jomol and the dyestuff/pharmaceutical preparation/cytostatic (e.g. actinomycine C, Sigma A4639 ®, Sigma, Munich, Federal Republic of Germany) are brought together in a polar solvent. Then an equimolar amount of a coupling agent (glutaraldehyde, Sigma G5882) is added in known manner and used for linking the components. The reaction temperature is 15° to 40° C. Then, chromatographic purification is carried out.

The production of the products tagged with a radioactive marker is carried out in known manner by reacting Jomol or a coupling product of Jomol or a solution with a salt solution of the radioactive marker and by obtaining the radioactive product in known manner, e.g. by column chromatography. Tagging with radioactive tracers is described in the literature.

Examples of radioactive tracers are the tracers which are customarily used in the field of treatment and diagnosis of malignant tumors, such as, for example, $^{99m}$technetium, $^{111}$indium, $^{123}$iodine, $^{125}$iodine, $^{130}$iodine, $^{131}$iodine, $^{132}$iodine and $^{224}$radium. The radioactivity can be, e.g., 5 μCi to 200 mCi.

When charging Jomol with a radionuclide, the peak of Jomol with an apparent molecular weight of 3000 in an FPLC elution pattern shows the maximum amount of the radionuclide. The same applies to Jomo-tech, Jomo-In and Jomo-Ra. In the case of Jomol-Sn-$^{99m}$Tc, Jomol-DTPA-$^{111}$In and Jomol-CE-$^{224}$Ra, after 5-day storage in aqueous solution 0.5 mg/ml at −20° C. after the labeling no autoradiolysis was detected.

According to the invention it is also possible to use mixtures of Jomol and its derivatives tagged with a radioactive tracer, a dyestuff or a cytostatic.

As according to the present invention, Jomol, its coupling products and the corresponding tagged derivatives, as described above, can be used on liposomes or in lipidized form.

Liposomes are spherical structures of one or more lipid double layers with an inner space. Such vesicles can be produced by extremely fine mechanical distribution of phospholipids, such as lecithin, in aqueous media.

According to the invention, liposomes are used which are single, unilamellar vesicles (SUV) and consist preferably of phosphatidyl choline:phosphatidyl serine:cholesterol in a molar ratio of 8:2:10 and are prepared by sonication. The lipids from which they are prepared are commercially available, for instance from Sigma Products. The lipids are dissolved in ether, purified by column chromatography, mixed with Jomol and/or its derivatives under $N_2$, suspended in phosphate-buffered saline solution (PBS), e.g. at a pH of 7.4, and then sonicated, e.g., for 25 minutes at $+2°$ C. with a pulsated Branson 15 sonicator. In general, the sonication is carried out under $N_2$.

After the sonication, the liposomes are chromatographed on a Sepharose 4 B column and the fractions of the population with radii less than 300 Å are preferably used (C. Huang, Biochemistry, 15, 2362 (1969)).

These liposomes are then tagged for diagnosis in known manner with preferably $^{99m}$technetium on the Jomol.

In order to check the radioactive labeling, an aliquot portion of the liposomes is introduced into a Sepharose 4 B column and chromatographed. It is found that the preparation has a specific activity of 99.2% of radioactivity bound to Jomol and 0.8% of free pertechnetate.

The liposomes can be charged with Jomol and/or its derivatives which are charged with a radioactive tracer, with a dyestuff, a cytostatic or mixtures of these compounds. Such liposomes are particularly suited for diagnosis.

According to an embodiment of the invention, charged Jomol or Jomol derivative is optionally—as explained above—dispersed in a lipid. The dispersing takes place by bringing the substances together and subjecting them to sonication, too.

As lipids one can use phosphatidyl choline alone or together with phosphatidyl serine and cholesterol, for example in a molar ratio of 8:2:10.

As mentioned above, it is known that a mixture of acetaldehyde and ethanol has a cancerotoxic effect. Surprisingly, it has now been found that Jomol or its derivatives develop a particularly good action when administered together with an adjuvant designated as a "cocktail". The adjuvant contains an aldehyde of formula I

RCHO      (I)

in which R is a hydrogen atom or a straight-chain or branched hydrocarbon group having 1 to 4 carbon atoms, and optionally an alcohol of formula II

$R^1CH_2OH$      (II)

in which $R^1$ has the meaning indicated above for R. The adjuvant optionally contains conventional excipients and/or diluents. It is especially preferred that the adjuvant contains an alcohol in addition to the aldehyde.

Surprisingly, it has been found that upon the simultaneous and time-staggered use of the adjuvant together with Jomol or Jomol derivatives, the efficiency of Jomol and/or Jomol derivatives is substantially improved.

Thus, the invention also relates to a product which contains the above-described diagnostic composition or pharmaceutical preparation and the above-described adjuvant.

The adjuvant in the product of the invention may contain the aldehyde as such in ordinary pharmacologically compatible excipients and/or diluents. It is particularly preferred to use the aldehyde in aqueous and/or alcoholic solution. According to the invention, it is particularly preferred in this connection to use the aldehyde in question together with its corresponding alcohol.

Preferred adjuvants liberate, directly or indirectly, and/or contain: formaldehyde/methanol, acetaldehyde/ethanol, n-propionaldehyde/n-propanol, iso-propionaldehyde/iso-propanol, n-butyraldehyde/n-butanol, iso-butyraldehyde/iso-butanol, tert-butyraldehyde/tert-butanol, n-valeraldehyde/n-pentanol or mixtures of these compounds.

In the required concentration and amount, the acetaldehyde/ethanol pair is virtually non-toxic; it can be administered in suitably high doses. From this there results the possibility of long-term treatment, even in combination with radiation treatment. The immunobiological system is influenced positively and a combination with other medicaments as well as with surgical and radiological measures is possible.

In addition to this ethanol/acetaldehyde mixture, other analogous mixtures of the above-mentioned type are also fundamentally possible. Methanol is metabolised substantially more slowly in the human body than ethanol, and propanol is metabolised two times faster than ethanol. The agent may in each case contain only one specific selected aldehyde, as well as mixtures of aldehydes. The use of aldehydes is not necessarily coupled with the presence of the corresponding alcohols. Aqueous solutions of the aldehydes can also be used. Instead of the free aldehydes, there may also be used in the invention those aldehyde derivatives which form the free aldehyde in the metabolism of the patient treated with the pharmaceutical agent of the invention. Suitable aldehyde derivatives are, for example, the acetals or semiacetals or condensation products, which may also be used as is or in dissolved form (water or alcohols) as well as in mixtures with the aldehydes and/or alcohols.

In another preferred embodiment of the invention, the adjuvant contains small amounts (less than 0.05% by weight) of peroxides, there entering into consideration, in particular, peroxides of related composition, especially $H_2O_2$ and/or aldehyde peroxide or hydroxy hydroperoxide, respectively, as well as the peroxide of the corresponding carboxylic acid. The anti-tumor action is still further improved by the content of peroxides.

The concentration of aldehyde in the preparation of the invention is determined, on the one hand, by its compatibility and, on the other hand, by the dose to be administered. For the pair ethanol/acetaldehyde, an acetaldehyde concentration in the alcohol of less than $2 \times 10^{-4}$ mole/liter is frequently unsatisfactorily slow in its action. The action increases with an increase in the concentration of aldehyde and its upper limit is formed in the individual case, as a rule, by incompatibility of the acetaldehyde which may possibly occur. In practice, for example, ethanol/aldehyde solutions with $5 \times 10^{-2}$ mole to 1 mole acetaldehyde per liter of ethanol have proven satisfactory, it being possible to use these mixtures in a dose of, e.g., 10 to 150 cm$^3$ per day.

It is preferred that the adjuvant contain 10 to 60 g of aldehyde per 1000 g of alcohol, especially preferred 40 g of aldehyde per 1000 g of alcohol. In general, the adjuvant is diluted with water for administration. The alcoholic solution may be diluted with any amount of water as desired. For example, one volume of the alcoholic solution can be diluted with 1 to 10 volumes, preferably with 2 to 5 volumes, of water.

The adjuvant is preferably administered orally in the form of aqueous solution and drunk by the patient. The adjuvant can, however, also be administered parenterally.

In the product or kit according to the invention, the two components can be combined in each case in different manner. The adjuvant can be present in a form suitable for oral administration and/or for parenteral administration, for example by infusion. The preparation of infusion solutions is well known to the person skilled in the art and can be effected in known manner. For example, the adjuvant may be present in the form of drink ampules or in the form of drink ampules which are diluted with water.

For diagnosis, it is preferred at first to administer the adjuvant as an aqueous solution orally and to administer the diagnostic parenterally, preferably intravenously, about 20 to 30 minutes later. For treatment, it is also preferred first to administer orally the adjuvant as described above and then the pharmaceutical preparation 20 to 30 minutes later. The pharmaceutical preparation is administered by inhalation, intravenously or intratumorally.

In general, the required Jomol dose for both treatment and diagnosis is 10 to 500 μg, whereby for diagnosis 10 to 50 μg are advantageously used as a dose administered only once and for treatment 10 to 500 μg are used daily. The duration of the treatment depends on the individual case. It is preferred to keep an individual dose in a bottle under sterile conditions. For administration, the bottle can, e.g., be diluted with saline solution for injection or introduced into a inhalation device.

The constituents of the kit are preferred to be in separate containers, whereby, e.g., the adjuvant may be present in a drink ampule or a screw-top bottle and the Jomol or one of its derivatives is present in a tightly sealed bottle or ampule.

Jomol and the Jomol derivatives are kept in a light-protective carton under nitrogen at $-40°$ to $-10°$ C. Exceptions are the Jomol preparations on liposomes or lipidized, which are kept at $+4°$ C. to $+10°$ C. The kit may contain a third container in which, e.g., a solvent is provided which is added to the Jomol and/or one of its derivatives shortly before the use. Solvents are all those that are pharmaceutically acceptable and dissolve Jomol and/or its derivatives, for example, physiological saline solution, PBS and others.

However, it is preferred to prepare the adjuvant by irradiating an alcohol of formula II

$$R^1CH_2OH \qquad (II)$$

in which $R^1$ is a hydrogen atom or a straight-chain or branched hydrocarbon group having 1 to 4 carbon atoms, with energy-rich radiation, with the admission of oxygen.

Gamma radiation, UV-radiation, X-radiation or electron radiation can be employed, for example, as energy-rich radiation. In this connection, the alcohols selected can be used as such but also alcohol/water mixtures, highly concentrated alcohol/water mixtures being particularly preferred as starting material. The irradiation is effected with admission of oxygen, and preferably with admission of air.

An anti-tumor agent which is particularly important and effective in practice can be prepared, for example, by exposing 96% ethanol in the presence of oxygen to energy-rich radiation of the type described until the desired amount of acetaldehyde has been formed. The solution then contains essentially, in addition to a large amount of ethanol, the acetaldehyde together with peroxides such as $H_2O_2$ or acetoperoxide or traces of peracetic acid as well as acetic acid. The last-mentioned substances substantially improve the action of the liposomes charged with Jomol and/or its derivatives. Surprisingly, it showed that an increase typical for ethanol-/aldehyde of the macrophages, T cells, T helper cells and killer cells was found and this effect deflects the direction of action of Jomol and its derivatives from a predominantly B cell stimulation, such as is known, to an increase of the macrophages, T cells, T helper cells and natural killer cells, so that previously unknown large numbers of these cells are produced in humans. This is not described in the above-mentioned literature reference by U. Ehrenfeld, and was also not obvious.

Jomol and its derivatives (in the present patent application, as "Jomol derivatives" are understood all the coupling products and tagged products) surprisingly easily pass through the cell walls, especially through the walls of lung alveoli, lymph and blood capillaries, and accumulate on cancer cells where they can easily be detected. This renders possible a new diagnosis and a novel way of treating malignant tumors, since the Jomol tagged with a radioactive marker and/or such Jomol derivatives get directly to the malignant tumor where they have the highest possible effect to detect and treat the tumor.

The diagnostic composition according to the invention can be used for the diagnosis of malignant tumors in vivo and in vitro. The malignant tumors can be diagnosed outside the body. For example, a surgeon can remove malignant tissue in an operation and then incubate the living tissue outside the organism so that in the flat, cut section of the tissue, e.g. upon color marking with fluorescein isothiocyanate, malignant tissue lights up in UV light and can be immediately distinguished from the dark, healthy tissue.

When the cocktail is applied by an infusion and after subsequently intravenous administration of Jomo-Color, tumor material becomes visible in UV light during an operation. In the case of a lymphogenous dissemination of tumor material, the tumor cells tagged with Jomol fluorescein isothiocyanate are rapidly phagocytised. With the agent according to the invention, it is possible to accurately characterize tumor sizes on the order of 100 to 10,000 cells; with additional administration of oxygen the agent is capable, on the basis of minimal radioactive radiation introduced for the diagnosis, to produce an active inflammation as a result of radiation destruction of tumor tissue.

According to the present invention it is thus possible for the first time to diagnose as well as to cure malignant tumors in mammals, particularly humans, in a simple manner without the patient being impaired. According to the invention, it is possible to irradiate the tumors in a well aimed fashion with practically no injury to neighboring tissue and, furthermore, one can, according to the invention, apply medication, for instance the cytostatics or immunmodulators, at the site where they are actually to act.

When Jomol and/or one of its derivatives is tagged with a radioactive tracer, the radioactive distribution is visualized by using an external gamma camera. Various melanosarcomas, squamous cell carcinomas and adenocarcinomas of the female breast are visualized with the external gamma camera. The tests can be reproduced.

Fluorescein isothiocyanate or $^{99m}$technetium remain bound to Jomol and/or its derivative at the cancer cell wall and are detectable there by fluorescence microscope or autoradiographically, respectively. When visualizing with the gamma camera, in the model with the Sprague-Dawley rat the binding rate of the substance claimed according to the invention to Walker carcinosarcoma 256 by simultaneously using the combination (cocktail) of ethanol/acetaldehyde/water is higher by 2.5 to 8 times than at the healthy tissue (when comparing the sides). In humans, the binding ratio is higher. Since Jomol is bloodspread in the body and passed via kidneys, liver and lungs to the urine, bile and expiratory air, in the case of corresponding labeling of Jomol and/or its derivatives with radioactive isotopes, in addition to cancer and its metastases in soft tissue and bones examinations of the function and/or clearance can also be carried out during these passages by means of a gamma camera display.

PHARMACOLOGICAL INVESTIGATIONS

1. Toxicity

Jomol and its derivatives are virtually non-toxic. In a Screening according to Robert A. Turner (carried out by the company Pharmatox, Sehnde, Federal Republic of Germany) no deviations from normal findings were found for Jomol, Jomotech, Jomo-In and Jomo-Color on SPF mice after an overdose which was calculated to be 4000 to 5000 times the daily human dose, i.e. in an amount of 2 mg/kg body-weight. The tolerance appears to be excellent, undesired side-effects did not occur.

2. Binding of radioactively tagged Jomol derivatives to malignant and benign cells in vitro In order to show that Jomol and its derivatives can be very easily bound to carcinoma cells, comparative tests were carried out. The binding behavior of the radioactive components Jomol-DTPA-$^{111}$In, Jomol-CE-$^{224}$Ra and Jomol-Sn-$^{99m}$Tc to carcinoma cells and healthy cells was tested in vitro. The carcinoma cells used were embryonal mice cells F9 and the healthy cells used were mice fibroblasts L929.

In a further test, it was shown that the binding is especially intensive when the cocktail according to the invention is administered prior to the administration of the radioactive components.

For evaluating the binding results, it is relevant that the volume of an average healthy fibroblast cell L929 is about three times as large as that of a malignant F9 cell, the surface thus being twice as large. In addition, the ratio of the cellular wall matrix and adhesion matrix to the cell is markedly higher for the healthy L929 cells than for the malignant F9 cells.

The result of the binding experiments is shown in the following Table I. Summarizing, it can be stated that the embryonal mice carcinoma cells F9 bind Jomol-DTPA-$^{111}$In, Jomol-CE-$^{224}$Ra and Jomol-Sn-$^{99m}$Tc better by a factor of about 30 to 60. A tendencial increase of the binding ratio by addition of the cocktail of alcohol and acetaldehyde can be seen.

TABLE I

Ratio of the specific cell labeling (cpm/$10^6$ disseminated cells, standardised) of embryonal mice carcinoma cells F9 to mice fibroblasts L929 (F9/L929)

| Binding medium | Jomol-DTPA-$^{111}$In | Jomol-CE-$^{224}$Ra | Jomol-Sn-$^{99m}$Tc |
|---|---|---|---|
| DMEM, 10% FCS | 34.2 | 28.6 | 30.6 | 12.6 |
| DMEM, 10% FCS 500 μg/ml EtOH | 42.0 | 33.6 | 49.2 | 33.6 |
| DMEM, 10% FCS 500 μg/ml EtOH 2 mM acetaldehyde | 56.4 | 28.0 | 62.4 | 33.6 |
| DMEM, 10% FCS 500 μg/ml EtOH 4 mM acetaldehyde | 150.0 | 48.6 | 44.4 | 26.4 |

DMEM, 10% FCS = Dulbecco's Modified Eagle Medium with 10% of fetal calf serum
EtOH = ethanol
L929 mice fibroblasts (ATCC CCL1, NCTC clone 929, connective tissue, mouse)
F9 embryonal mice cancer cells, H2 negative, line 129, laboratory F. Jakob, Institut Pasteur, Paris

3. Binding of the radioactively tagged Jomol to malignant tumor tissue in vivo a) Binding to Walker carcinosarcoma 256 in the Sprague-Dawley rat 4 days after subcutaneous transplantation of Walker carcinosarcoma 256, 0.8 ml of a Jomol-DTPA-$^{111}$In solution or a Jomol-Sn-$^{99m}$Tc solution each were applied to 3 female Sprague-Dawley rats. The first solution contained about 80 nmol/ml of Jomol-DTPA-$^{111}$In in a specific radioacitivity of about 7 Ci/mmol. The second solution contained about 68 nmol/ml of Jomol-Sn-$^{99m}$Tc in a specific radioactivity of about 25 Ci/mmol. 30 minutes prior to the i.v. administration of the tagged Jomol, all animals were orally administered 1 ml of cocktail (cocktail: 22.5 ml of physiological saline solution, 2.4 ml of ethanol, 0.26 ml of acetaldehyde). 24 hours after the application, the animals were szintigraphed from a dorsal view in chloral hydrate anesthesia.

In all animals, the tumor could be clearly defined. The tumor labeling given as quotient of the specific accumulation in tumor and muscle tissue resulted in between 4:1 and 8:1 for Jomol-DTPA-$^{111}$In and between 4:1 and 6:1 for Jomol-Sn-$^{99m}$Tc. In other follow-up experiments, binding ratios of 8:1 were found quite frequently, and in few cases even up to 36:1.

b) Distribution of Jomol-Sn-$^{99m}$Tc in the tumor-bearing Sprague-Dawley rat 4 days after subcutaneous transplantation of Walker carcinosarcoma 256 into the right side, 0.5 ml of a Jomol-Sn-$^{99m}$Tc solution each was injected into the caudal veins of five female Sprague-Dawley rats. The solution contained 25 mmol/ml of Jomol-Sn-$^{99m}$Tc in a specific radioactivity of 25 Ci/mmol. 30 minutes before the application, the animals were orally administered 2.5 ml of cocktail (cocktail: 22.5 ml of physiological saline solution, 2.4 ml of ethanol, 0.26 ml of acetaldehyde).

In the scintigram, for two of the animals a binding ratio (specific accumulation in the tumor to specific accumulation in the muscle tissue) of 6:1 was obtained with a means tumor weight of about 1.5 g. Scintigraphically, the tumor could be defined 30 minutes after the application. Extrapolated to human standards it can be expected that here tumor scintigraphy will be possible as soon as 3 hours after application. For detecting the distribution in the organs, the animals were decapitated one hour after the injection and largely exsanguinated. The organs indicated in Table II were extracted and weighed; the radioactivity contained therein was measured in a gamma counter.

The following Table II shows the distribution of the radioactivity one hour after application.

A not inconsiderable portion of the radioactivity was renally excreted within one hour; the estimated clearance is 0.5 ml/min.

TABLE II

In vivo distribution of $^{99m}$Tc-Jomol in the tumor-bearing rat one hour after intravenous application (n = 5, Sprague-Dawley. Walker carcinosarcoma 256)

| organ | % of the dose/g |
| --- | --- |
| blood | 0.46 ± 0.01 |
| liver | 0.17 ± 0.05 |
| spleen | 0.09 ± 0.01 |
| stomach | 0.14 ± 0.02 |
| kidneys | 3.34 ± 0.29 |
| heart | 0.16 ± 0.02 |
| lungs | 0.24 ± 0.02 |
| muscle | 0.05 ± 0.01 |
| thymus | 0.11 ± 0.04 |
| femur | 0.09 ± 0.02 |
| tumor | 0.32 ± 0.05 | c) In man, various malignant tumors were visualized. By means of a gamma camera, 3 hours after intravenous administration of Jomo-tech (20 mCi $^{99m}$technetium) or Jomo-In (2 to 3 mCi $^{111}$indium) (in most cases half an hour before a dose cocktail—24 ml of ethanol, 1 ml of acetaldehyde, 225 ml of water—was administered orally) the tumors were visualized. At the location of the tumor display, the tumor was verified by other investigations (e.g. histologically). The ratio tumor area/non-tumor area was above 10:1, in the liver above 8:1, with respect to the radiation detected by the gamma camera.

4. Therapeutic effect of Jomol-CE-$^{224}$Ra 3 days after subcutaneous transplantation of Walker carcinosarcoma 256 into the thigh, 1 ml of a solution with Jomol-CE-$^{224}$Ra each was injected into the caudal veins of 22 Sprague-Dawley rats (0.8 Ci/mmol, 13 nmol/ml). 30 minutes prior to the application, the animals were orally administered 2.5 ml of cocktail (cocktail: 22.5 ml of physiological saline solution, 2.4 ml of ethanol, 0.26 ml of acetaldehyde).

Depending on the problem, the animals were either killed from the 3rd day of application on or they died after the 8th to 10th day. The tumors were extracted and weighed. The correlation 1 g tumor weight/time after application was subjected to a regression analysis and compared with a corresponding correlation of untreated animals.

The tumor development in the exponential growth phase can be described after single dose of Jomo-CE-$^{224}$Ra by a straight line of the form 1 g y=0.19× −0.66.

The development of untreated tumors (corresponding to "Tumor Steckbrief"), DKFZ Heidelberg, Federal Republic of Germany) can be described by a straight line of the form 1 g y=0.28× −1.28. As compared therewith, the growth in the treated group has been reduced by about 30%.

5. Behavior of $^{131}$iodine-Jomol, autoradiography of tumor cells of a Walker carcinosarcoma 256 on a male Sprague-Dawely rat 4 days after intravenous application preparation: 281 μCi $^{131}$iodine/μmol Jomol
used dose: 30 μCi $^{131}$iodine, bound to Jomol
molar ratio: $^{131}$J-Jomol/Jomol untagged as 1:1.3×10$^4$
duration of experiment (preparation until end of autoradiography): 8 days (3 days of which autoradiography)
weight of the SD-rat: about 200 g
cell number of the SD-rat: about 6×10$^{11}$ (estimated for 200 g body-weight)

In the case of statistical distribution, 7 molecules of $^{131}$J-Jomol per cell of the SD-rat are to be expected after i.v. application. After 4 days and an excretion in the urine of the rat of about 1 nmol of iodine daily, less than 10$^{-8}$ of a given dose of 14 pmol of $^{131}$J is present. After expiration of a half-life since preparation, 10$^{-8}$ of 14 pmol of $^{131}$J result in 7 atoms of $^{131}$iodine per 10$^{11}$ cells. Per cell of the visualized cut of the Walker carcinosarcoma 256 of the SD-rat autoradiographic disintegration of $^{131}$iodine of >1 is found with an autoradiography lasting 3 days.

In a molar ratio as was given in the applied dose, >5×10$^4$ binding positions for Jomol per cell can be calculated. A decrease of tumor-bound $^{131}$J-Jomol cannot be observed within the duration of test.

6. Immunostimulatory effect of cocktail and Jomol (and/or Jomo-Aer) in humans As has already been stated, Jomol leads to an increase in the cellular immune defense in humans, especially together with the cocktail (combination as according to the invention).

When using the cocktail of 50 g of 96% ethanol, 2 g of extremely pure acetaldehyde and 450 g of water, orally, and inhalation of Jomol on liposomes of phosphatidyl choline, phosphatidyl serine and cholesterol in the molar ratio of 8:2:10 in physiological saline solution, optimum effects show for a dose of 30 to 60 μg of Jomol (on 5 mg of liposomes in 5 ml of physiological aqueous saline solution).

Hereinafter, the effects are shown by means of a case description. In this case, Jomol-Aer was nebulised with a Siemens-Micro-Inhalator and inhaled. The cocktail was administered previously.

Blood Picture Evaluations

In previously present normal values, for example, 7400 leucocytes/μl, monocytes, T lymphocytes and B lymphocytes in the normal range, 24 hours after application the values rise to, e.g., 24,800 leucocytes/μl. The lymphocytes reach the following values:

| | per μl |
| --- | --- |
| T lymphocytes, total: | |
| via E-rosettes | 11,840 |
| via monoclonal antibodies | 12,640 |
| T helper cells via monoclonal antibodies | 8,960 |
| T suppressor cells via monoclonal antibodies | 2,560 |

-continued

|  | per μl |
|---|---|
| and via cytotoxic monoclonal antibodies | |
| T helper/T suppressor cytotoxic = 3.5 | 1,600 |
| B lymphocytes Ig surface-positive | |
| monocytes via monoclonal antibodies | 2,400 |
| lymphocytes Ia+ (activated B and T lymphocytes and some monocytes) via monoclonal antibodies | 1,120 |
| OKT 11 | 13,760 |
| Leu 7 | 2,240 |

Response of the lymphocytes to mitogens (results of the isotope measuring, cpm):

|  | cpm ± e.s. |
|---|---|
| PHA: | 86,578 ± 4,768 |
| ConA: | 87,536 ± 6,755 |
| without mitogen (controls): | 309 ± 118 |

In general, it is to be stated that the increase of the cellular immune defense in humans, as was observed for months and years in the example of the monocytes, cannot be depleted. Apart from the usual slight physiological variations, always a clear increase in the number of granulocytes per μl—in young people by more than 3,000/μl, in old people by about 1,500/μl—and an increase in the number of monocytes from the normal values 0 to 140/μl up to about 2,000/μl blood (in old people up to about 900 to 1000/μl) has been achieved by using the agent claimed according to the invention, termed "Jomol".

7. On the diagnostic/therapeutic effects of Jomo-Color (Jomol fluorescein isothiocyanate) (Jomol-Fitc)

From tests with Fitc-tagged lymphocytes, it has been known that they are phagocytised in vivo within few hours. Polymorphonuclear leucocytes (granulocytes) have proteolytic enzymes and lysozyme. The lysozme serves for splitting murein in bacteria.

Surprisingly, it has now been found that the Fitc-"alienated" murein fragment Jomol (in cocktail administration enhanced) when bound to tumor cells effects granulocyte invasions in the area of the cell wall matrix changed by proteases. When Walker carcinosarcoma 256 ascites is treated with Jomol-Fitc, ethanol/acetaldehyde and p-hydroxyphenyl-α-ketopropionic acid antagonists (acting by competition to their receptor) or tyrosine-analogous molecules and monoaminooxidase inhibitors on Sprague-Dawley rats, after 24 hours, e.g. after use of Jomol-Fitc, ethanol/acetaldehyde and cotrimoxazole, a very large number of leucocytes is found in the punctate of the ascites and a subtotal regressive change of the ascites tumor cells.. The controls show vital tumor cells and sparsely leucocytes. Examples of the above-mentioned tyrosine-analogous and tyrosine decomposition product antagonists are sulfamethoxazole and isoniazid with the monoaminooxidase inhibitor tranylcypromine.

Like the selectively occurring fluorescence of the cancer cell walls, this effect can be observed (fluorescence)microscopically already after 10 to 15 minutes after the i.v. application of Jomo-Color. In 7 tests with a total of 131 Sprague-Dawley rats (with 2 to 3 g of Walker carcinosarcoma tumor each), after i.v. administration of about 30 μg of Jomol-Fitc per animal, a subtotal to total colliquation of the tumor was found in about one third of the animals 24 to 48 hours after application. In the other animals, this process could not be clinically observed.

The following examples explain the invention.

EXAMPLE 1

Production of Jomol

Nocardia opaca (ATCC 21 953) are cultivated on DST plates (Oxoid, Wesel, Federal Republic of Germany) or on glucose agar, 2% (Merck, Darmstadt, Federal Republic of Germany) in plate technique on three to four plates for 5 to 8 days. After collecting, the bacteria are inoculated in about 100 ml of ordinary nutrient broth and incubated at 30° to 37° C. over night.

The Nocardia bacteria are preferably collected by centrifugation, e.g. at 4000 rpm, in the "Roto-Silenta-K"-Hettich refrigerated centrifuge (or other suitable ones) having a rotor of 40 cm in diameter for 5 to 10 minutes. The resulting sediment (about 5 g of bacteria) is suspended in 100 ml of, e.g., 0.01M tris-HCl buffer (pH 7.4), preferably with EDTA-Na$_2$ (0.06%) (washing step), as mentioned above, separated by centrifugation and suspended in about 100 ml of 0.01M tris-HCl buffer of a pH of 7.4 with preferably 0.06% EDTA-Na$_2$ and with 10% of glucose. After about 30 minutes, 10 mg of lysozyme (Lysozyme, Sigma L-6876, Sigma, Munich, Federal Republic of Germany) and preferably for reducing the viscosity 3 mg of deoxyribonuclease (Deoxyribonuclease, Sigma D-0876) are added. This phase with glucose and ferments lasts 2 hours and takes place at between 30° and 37° C. Then, as indicated above, separation by centrifugation can be effected. The sediment can be resuspended in 100 ml of 0.01M tris-HCl buffer with 0.06% EDTA-Na$_2$ and again be separated by centrifugation and resuspended in the same medium. This washing step may be omitted, however, it serves to remove more bacterial wall material and nutrient broth from the concludingly used supernatant.

Then, the cells are destroyed. This can be done by all suitable methods, ultrasonication for 1 minute, e.g. with the "Sonicator cell disruptor" from Kontron Ultrasonics, type W 185 F, 15 mm end range, step 3, scale at 50, being preferred.

Then centrifugation is carried out in the refrigerated centrifuge (as described above) at 4000 rpm at 4° to 6° C. for 10 to 15 minutes.

The UV spectrum of the supernatant is shown in FIG. 1.

The supernatant is preferably divided into five portions and each of five prepared Sephadex-G-75 columns is supplied with one portion thereof. The columns are 80 cm long, inner diameter 2.5 cm, the Sephadex filling height is 60 cm (UV detection at 214 nm). When using one column, the other portions are frozen at −25° C. until they are used. The fraction has about 4500 to 900 daltons. In elution, it passes through e.g. with 0.01 M tris-HCl buffer (pH 7.4) with 0.06% EDTA-Na$_2$ at about 900 to 980 ml, at a drop rate of about two drops per second (over night) after about 12 hours in 1 to 2 hours. This fraction contains the active fraction, i.e. the desired product 2b*. Then lyophylisation takes place. Thereafter, incubation is effected preferably at 80° C. for 1 hour.

If lyophilisation is not effected, the dilute solutions will have to be kept in a frozen condition at −20° C., or even better at −40° C. or −80° C.

Jomol is obtained by reacting fraction 2b* (assumed mean molecular weight: 4000) with acetaldehyde in a molar ratio of 2b*: acetaldehyde of 1:2. Then lyophilisation has to be carried out again, optionally (see above) frozen.

About 5 g of bacteria yield about 2 mg of pure product, i.e. Jomol. The product is very hygroscopic, weighings under access of humidity (air) do not permit exact indications of substance amounts, therefore, weighing is to be effected in the previously weighed closed vessel after freeze-drying, and optionally determining the water content of the lyophylisate is to be carried out by means of conventional methods. The Jomol shows the UV spectrum illustrated in FIG. 2. It has the following properties:

Absorption maximum in the UV spectrum at 282.5 nm. A spectrophotometer UVIKON 860 (1984), Kontron, Zürich, Switzerland, was used and the substance was dissolved in water, reference water 1 cm quartz cells;

Apparent molecular weights at 4500, 3000 and 900;

depending on the residual water content of ivory color, amorphous-crystalline-flaky;

pH value of 5.5 (1 mg of the compound, dissolved in 1 ml of water);

slightly positive, pink ninhydrin reaction;

stainable with orcine reagent;

peptide portion; about 50%, based on the amorphous substance (protein test MicroBioRad according to L. Thomas, J. Clin. Chem. Clin. Biochem., Vol. 19, 1981, pages 203 to 208, company: BioRad, Munich; Coomassie brilliant Blue G 250 ®);

the following $R_f$ values (solvent indication volume:volume)

| | | |
|---|---|---|
| $R_f = 0.20$ | (butanol:glacial acetic acid:water | 4:1:1) |
| $R_f = 0.45$ | (benzene:glacial acetic acid:water | 2:1:2) |
| $R_f = 0.685$ | (methanol:glacial acetic acid:water | 4:1:1) |
| no migration | (chloroform:methanol | 96:4) |
| $R_f = 0.54$ | (chloroform:methanol | 1:1); | solubility: poor solubility in non-polar solvents, very good solubility in polar solvents;

identifyable constituents:

| substances | ratio (approach) |
|---|---|
| neutral sugars (glucose, galactose, ribose) | ($\leqq$)1 |
| amino sugars (glucosamine, muramic acid) (after hydrolysis) | 3.5 |
| amino acids (ala, glu, iso-gln, gly, lys, DAP) | 4 |
| lipids | <1 |
| phosphorus | <1 | structure: peptidoglycan structure, the glycan skeleton of which consists of 10 to 80 disaccharides of N-acetylglucosaminyl-N-acetylmuramyl.

EXAMPLE 2

Production of the Adjuvant "Cocktail"

1000 ml of ethanol 96% and 40 g of hyperpure acetaldehyde are mixed.

An active dose is 25 ml thereof.

Application instructions:

25 ml of the cocktail are mixed with 225 ml of water and administered orally.

The daily dose is 2 to 3 active doses, the dose may be increased by order of a physician.

With suspected cerebral metastases, the cocktail is not allowed to be administered.

Production Examples of Jomol Derivatives

EXAMPLE 3

Jomol-Sn (also termed Jomo-tech)

(a) general working conditions: Work under nitrogen at 0° to 10° C., solutions are to be blown through with nitrogen prior to their use, used reaction vessels washed with acid.

(b) 20 mg of Jomol are dissolved in 100 $\mu$l of 1 n HCl and then the solution is set aside for 10 to 15 minutes. Then, 1 mg of $SnCl_2 \times 2\ H_2O$ (solid) is added and the reaction mixture is set aside for about 20 minutes. 2 ml of a 0.1 n HCl, physiological saline solution with 50 $\mu$g of $FeCl_2 \times 4\ H_2O$ (0° to 1° C.) are added.

After vigorous stirring, 20 $\mu$l portions of the solution are filled into pre-cooled phials for piercing located on a refrigerated storage surface at a temperature of $-10°$ to $-20°$ C. The phials for piercing are closed immediately and kept in frozen condition (about $-20°$ C.) until they are used.

EXAMPLE 4

Jomol-Sn charged with $^{99m}$technetium for diagnosis

In order to tag with $^{99m}$technetium, 20 to 100 mCi $^{99m}$Tc in a volume of up to 5 ml is added to the frozen phial for piercing (Example 3) (from a $^{99m}$molybdenum generator, Squibb von Heyden, Regensburg, Federal Republic of Germany). It is preferred to use the second eluate of the preparation day. After 10 to 15 minutes at room temperature (avoid direct light), the preparation can be used for i.v. injection for a diagnostic test with the gamma camera.

EXAMPLE 5

Jomol-Sn lyo (also termed Jomo-tech lyo), suited for charge with $^{99m}$technetium for diagnosis (a) general working conditions: work under nitrogen, use reaction vessels after washed with acid.

(b) 6 mg of Jomol, lyophilised in 10 mM tris-HCl buffer, pH 7 to 7.5, are dissolved in 100 $\mu$l of 1 n HCl and set aside at room temperature for about 15 minutes. Then, 0.3 mg of $SnCl_2 \times 2H_2O$ are dissolved in 100 $\mu$l of 1 n HCl and added to the Jomol solution. Then, it is set aside at room temperature for about 20 minutes.

(c) 0.6 mg of sodium acetate, 3.4 mg of succinic acid and 50.0 mg of lactose are dissolved in 60 ml of physiological saline solution at 0° C. 0.8 ml of this solution are added to the Jomol solution obtained according to item (b). A final volume of 1 ml results.

Single doses of 100 $\mu$l each are distributed in 10 pre-cooled phials for piercing on a $-10°$ to $-20°$ C. cold storage surface. Then the phials are subjected to lyophilisation, closed under nitrogen and kept at $-20°$ C. until they are used.

Note: the above-mentioned solutions are used blown through with nitrogen.

EXAMPLE 6

Jomol-Sn lyo charged with $^{99m}$technetium

Labeling with $^{99m}$technetium is effected in the same manner as described in Example 4.

EXAMPLE 7

Coupling product of Jomol and diethylenetriamine pentaacetic acid

This coupling product is suited for charge with $^{111}$indium or with $^{99m}$technetium reduced by $SnCl_2$.

(a) general working conditions: The reaction vessels are used after being washed with acid. Operations are done under nitrogen at 0° to 10° C., the solutions used are blown through with nitrogen.

(b) 5 mg of diethylenetriamine pentaacetic acid anhydride are suspended in 5 ml of absolute diethylether (this suspension is termed Sl).

(c) About 200 μg Jomol are dissolved in 300 μl of bicarbonate buffer (0.05M, pH 7.0) in physiological saline solution. Under vigorous stirring (mixer, 30 to 60 seconds) 25 μl of the suspension Sl are added and then incubation is carried out at 37° C. for 1 hour. During this operation, the ether evaporates.

Then, chromatography is effected:

FPLC chromatography column: Superose 12, HR 10/30, Code-No. 17-0538-01, Pharmacia, Freiburg, Federal Republic of Germany.
Applied volume: about 300 μl
eluent: physiological saline solution
flow rate: 1 ml/min
detection: λ=214 nm, Uvicon 820, Kontron,
HPLC pump: LC pump 410, Kontron, Munich, Federal Republic of Germany.

In the product fraction, the Jomol is completely present as Jomol-DTPA. The bond of the DTPA to the amino group of the lysine of the Jomol is stable, other bonds hydrolyse.

EXAMPLE 8

Labeling of Jomol diethylenediamine pentaacetic acid with $^{111}$indium

About 2 mCi $^{111}$indium in 0.2 ml of 40 mM HCl are added to about 220 μg of Jomol diethylenetriamine pentaacetic acid (termed hereinafter Jomol-DTPA) in 3 ml of 5 mM bicarbonate buffer (pH 7.0) in physiological saline solution. After swirling and setting aside at room temperature for 15 minutes, the resulting solution can be used for intravenous injection (i.v.). The examination is carried out with a gamma camera.

Figure 4:
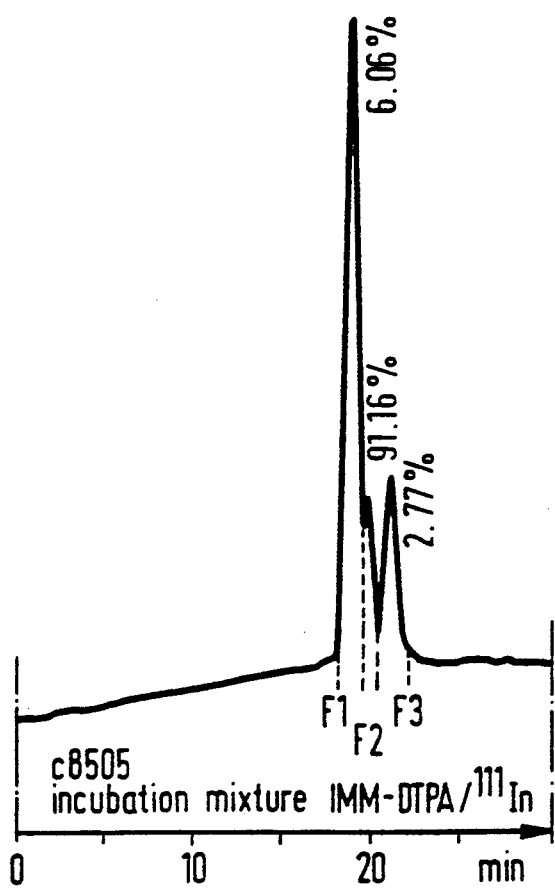

With FPLC chromatography (214 nm, 0.1M phosphate buffer), the Jomol-DTPA tagged with $^{111}$In leads to the elution pattern shown in FIG. 4. The diagram gives the distribution of the radioactivity on three separable fractions.

EXAMPLE 9

Labeling of Jomol diethylenediamine pentaacetic acid with $^{99m}$technetium

For tagging with $^{99m}$technetium, 100 μl of a hydrochloric (0.1 n HCl) 3 mM $SnCl_2 \times 2H_2O$ physiological saline solution stabilized by 0.1 mM of $FeCl_2 \times 4H_2O$ is added to 1 ml of Jomol-DTPA solution (about 50 μg) (frozen) and set aside for 10 minutes. Then 20 to 50 mCi of $^{99m}$technetium in a volume of up to 5 ml are added (from the second eluate of the day of preparation). After 10 to 15 minutes, the preparation can be used for i.v. injection and testing for tumors with the gamma camera.

EXAMPLE 10

Jomol tagged with radioactive iodine

Jomol is iodinated by the modified chloroamine T method at 0° to 5° C.

250 μg Jomol, lyophilised in 10 mM $NH_4$ acetate, are dissolved in 60 μl PBS (0.25M, pH 7.5). Then, 1 mCi $^{131}$J (Amersham-Buchler, Braunschweig, Federal Republic of Germany) in 25 μl is added and then 53 μg chloroamine T (N-chloro-p-toluene-sulfonamide-$Na \times 3H_2O$, Serva, Heidelberg, Federal Republic of Germany, 16784) in 15 μl PBS (0.25M). After about 30 seconds 90 μg Na-metabisulfite in 20 μl PBS (0.25M) is added.

Thereafter, chromatography on Sephadex G 25 (column bed 6 cm × 0.6 cm, eluent 0.1 n acetic acid, column equilibrated with about 50 μg Jomol) is effected. The yield is about 80%.

EXAMPLE 11

Production of Jomol Coupling Products (a) Jomol-Uridin (Jomo-J/U)

The production is carried out analogously to the binding of diethylenetriamine pentaacetic acid, as described in Example 7.

30 μg of uridine-2',3'-dialdehyde are dissolved in 10 μl dried diethylene ether (uridine-2',3'-dialdehyde, Sigma, U 0128). The resulting product is chromatographed as described in Example 7.

(b) Jomol-L-Tyrosin (Jomo-J/TS)

The coupling product is produced in the same manner as described in Example 7, α-amino-β-[p-hydroxyphenyl]propionaldehyde being used in an amount of 30 μg in 10 μl of absolute diethylether.

(c) Jomol-L-Thyronin (Jomol J/Tn)

α-amino-β-[p-hydroxyphenyl(p-hydroxphenyleether)]propionaldehyde is bound in the same manner as described in Example 7.

EXAMPLE 12

Production of a iodine-tagged coupling product of Jomol-Uridin/Jomol-L-Tyrosin/Jomol-L-Thyronin/Jomo-Color The coupling product produced according to Example 11 (a) of Jomol and uridine is carried out with a suitable radionuclide according to the process conventional for uridine by capable laboratories (e.g. Amersham, Great Britain).

The coupling products produced according to Examples 11 (b) and 11 (c) and Jomo-Color (see Example 15) are tagged with the radioactive iodine according to the process indicated in Example 10.

EXAMPLE 13

Jomol bound to a precursor of the Kryptofix (termed Jomo-Ra or Jomol-CE)

1 ml of 0.2M borate buffer (pH 8.0) is added to 200 μl of an aqueous solution of 1 mg Jomol. A solution of a precursor of the Kryptofix is prepared separately. The precursor is termed CE and can be obtained from Merck, Darmstadt. The CE has the following formula:

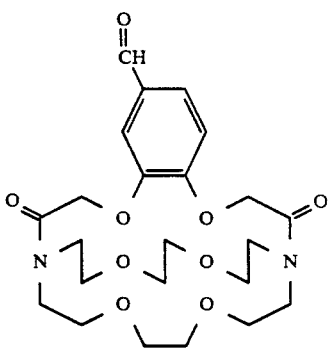

The solution has a concentration of 1 mg per ml ethanol.

240 μl of the ethanolic CE solution are added to the above Jomol solution. 160 μl of cyanoborohydride solution (1 mg/ml 0.2M borate buffer, pH 8.0) are added to the reaction mixture. The reaction mixture is incubated at 37° C. for 20 hours and can then be used directly for binding of radioactive marker.

EXAMPLE 14

Labeling of Jomol-CE with radioactive radium

After the above-mentioned incubation, $^{224}$radium as $^{224}$RaCl$_2$ solution (Amersham/Buchler, Braunschweig, Federal Republic of Germany) up to 200 μCi are added to the reaction mixture and set aside at room temperature for about 1 hour. The resulting solution is applied to a Superose$^7$H-FPLC column (Pharmacia, Freiburg, Federal Republic of Germany). The eluent used is 50 mM potassium phosphate buffer of a pH of 6.8 in physiological saline solution, 1 ml/min. Detection at 214 nm, and radioactivity monitoring (flow monitor, Berthold, Wildbad, Federal Republic of Germany).

The reaction product and free Jomol (0.5 mg/ml water) mainly show the same spectrum. The fractional removal permits the separation of the low-molecular components of the reaction mixture. The product is eluated in 2 peaks. After about 80% of the applied radioactivity has been eluted, a shoulder becomes visible at the 2nd peak. The fractions to be assigned to this shoulder and the subsequent ones are discarded. They contain, among other things, the cyanoborohydride.

Since Jomol-CE-$^{224}$Ra is not only accumulated on cancer cell surfaces (whereby about 1 g of cancer tissue will be destroyed upon i.v. administration of about 5 μCi), but also, like the immunostimulating pure immune modulator molecule, penetrates into monocytes, macrophages, microphages and bone marrow stem cells, prior to the i.v. administration of Jomol-CE-$^{224}$Ra care must be taken that these cells cannot take up the product. A restriction of the uptake of Jomol-CE-$^{224}$Ra in immunocompetent and bone marrow stem cells is required prior to the administration of the activity by high doses of cortisol i.v./i.m. at intervals known to the person skilled in the art. Further steps have to be taken ad hoc by consulting an immunologist. If this is not done, the danger of leukemia will be given. The medicament should mainly be used after micro-dissemination of tumor cells by operation (not in the case of non-Hodgkin tumors).

EXAMPLE 15

Jomol fluorescein isothiocyanate (Jomo-Color) for diagnosis and/or treatment working conditions:
  room temperature
  fluorescein isothiocyanate in saturated solution in ethanol 96%
  Jomol 100 mg dissolved in 200 μl H$_2$O.

Jomol and fluorescein isothiocyanate are brought together in a molar ratio of 1:5 and mixed in ultrasound for 30 seconds. Then, the mixture is set aside for 10 minutes and fractionated on a column 30 cm×0.6 cm, column bed 15 cm Sephadex G 75, eluent physiological saline solution 0.5 ml/min. Fraction 2.5 to 9 ml contains Jomo-Color. The column is to be previously equilibrated by 2 runs with 5 mg Jomol-Fitc.

The resulting fraction is either frozen immediately at −20° C. or portioned per 300 μg Jomol-Fitc and lyophilised, closed under nitrogen and kept at −20° C. until it is used.

EXAMPLES OF KITS AND THEIR APPLICATIONS (1) Jomol kit for immunostimulation constituents:
  (a) cocktail (ethanol 96%, 50 g/hyperpure acetaldehyde, 2 g) 2×1 dose, screw-top bottle
  (b) Jomol (300 to 600 μg lyophilisate≐30 μg dry substance) 1 dose, phial for piercing
  (c) physiological saline solution (5 ml) solvent for Jomol ampule application instructions:
  for (a) Cocktail: (not in the case of cerebral metastases) 1 dose=25 ml of the screw-top bottle, dilute cocktail with 225 ml water and administer orally; after 30 min. the Jomol solution (for (b)) is administered intravenously.
  for (b) Jomol: the physiological saline solution is taken up from the ampule (c) in a syringe and supplied to the phial for piercing (b). After dissolution of the lyophilisate Jomol by swirling of the phial, the solution is again taken up in the syringe and injected intravenously to the patient.

(2) Jomol-Aer-Kit for immunostimulation per inhalationem constituents:
  (a) Cocktail (see (1a))
  (b) Jomol (see (1b))
  (c) physiological saline solution, 5 ml, phial for piercing, containing liposomes, 5 mg, consisting of phosphatidyl choline:phosphatidyl serine:cholesterol in a molar ratio of 8:2:10 application instructions:
  for (a) cocktail (see (1a))
  for (b) and (c) The phials for piercing (b) and (c) are connected with a double cannula, the contents of (c) flows into (b). The phial (b) is shaked, the contents is supplied to a inhalator vessel and inhaled, e.g., with a Siemens-Micro-Inhalator.

(3) Jomo-tech, kit for the scintigraphic display of malignant tumors with the gamma camera constituents:
  (a) cocktail (see (1a))

(b) Jomo-tech (200 μg Jomol-Sn ≙ 20 μg dry substance, containing Jomol + 10 μg $SnCl_2 \times 2H_2O$ + 0.5 μg $FeCl_2 \times 4 H_2O$ in 0.1 n HCl of physiological saline solution), phial for piercing, frozen at −20° C.

application instructions:
for (a) cocktail (see (1a))
for (b) Jomotech: 20 to 30 mCi $^{99m}$technetium in physiological saline solution (2nd eluate of the day of preparation from a $^{99m}$molybdenum generator), in a volume of up to 5 ml, are supplied to the frozen phial (b) by means of a syringe which is not removed. The phial (b) is swirled several times, set aside at room temperature for 10 to 15 minutes, then intravenous injection is carried out.

(4) Jomo-tech lyo, kit for scintigraphic display of malignant tumors with the gamma camera constituents:
(a) cocktail (see (1a))
(b) Jomo-tech lyo (1350 μg Jomol-Sn ≙ 813 μg dry substance, containing Jomol + 30 μg $SnCl_2 \times 2 H_2O$ + 8 μg Na-acetate + 45 μg succinic acid + 670 μg lactose), lyophilised, phial for piercing, frozen at −20° C.

application instructions:
see (3) Jomo-tech (5) SmiL-N/Tc, kit for scintigraphic display of malignant tumors of the lungs with the gamma camera constituents:
(a) cocktail (see (1a))
(b) Jomo-tech (see (3b))
(c) liposomes in physiological saline solution (see (2c))

application instructions:
for (a) cocktail (see (1a))
for (b) Jomo-tech (see (3b)). Instead of the intravenous injection it is instilled into the phial (c).
for (c) contents of (b) and (c) are brought together, swirled and inhaled with a closed inhalation system.

(6) Jomo-In, kit for scintigraphic display of malignant tumors with the gamma camera constituents:
(a) cocktail (see (1a))
(b) Jomo-In (200 μg Jomol, dry, +20 μg DTPA = 220 μg Jomol-DTPA in 3 ml of physiological saline solution, 5 mM Na-bicarbonate buffer, pH 7.0), phial for piercing, frozen at −20° C.

application instructions:
for (a) cocktail (see (1a))
for (b) Thaw Jomo-In and add 2 to 3 mCi $^{111}$indium in 0.2 to 0.3 ml 40 mM HCl ($InCl_3$). After swirling and setting aside at room temperature for 15 minutes, the resulting solution can be used for an intravenous injection for test with the gamma camera.

(7) Jomo-J, tagged with $^{131}$iodine, kit for scintigraphic display of malignant tumors with the gamma camera and for treatment constituents:
(a) cocktail (see (1a))
(b) Jomo-J, tagged with $^{131}$iodine (about 250 μg Jomol ≙ 25 μg Jomol dry substance + 1 mCi $^{131}$iodine) in 1 to 2 ml PBS, 25 mM, 0.05 n acetic acid, phial for piercing, frozen at −20° C.

application instructions:
for (a) cocktail (see (1a))
for (b) Thaw Jomo-J, tagged with $^{131}$iodine and inject intravenously, then the test with the gamma camera follows.

Blocking of the thyroid gland with sodium perchlorate is recommended.

For treatment, optionally higher doses are used by order of the physician in charge.

(8) Jomo-Ra, tagged with $^{224}$radium, kit for local radiation treatment of micro-disseminations of cancer cells (Jomol-CE-$^{224}$Ra for i.v./i.t.)

constituents:
(a) cocktail (see (1a))
(b) Jomol-CE-$^{224}$Ra (about 30 μg Jomol-CE dry substance, tagged with 200 μCi $^{224}$radium) in 2 ml PBS, 25 mM, phial for piercing, frozen at −20° C.

application instructions:
for (a) cocktail (see (1a))
for (b) Jomol-CE-$^{224}$Ra:
Two hours before the treatment with Jomo-Ra 250 mg cortisol is administered i.v., then cocktail orally, then thawing (b) and applying intravenously or intratumorally.

(9) Jomo-Color, kit for the color diagnosis with ultraviolet light during the operation and for treatment in the case of malignant tumors constituents:
(a) cocktail (see (1a))
(b) Jomol fluorescein isothiocyanate (about 300 μg dry substance, contains Jomol:fluorescein isothiocyanate in a molar ratio of 1:5) lyophilised in 5 ml physiological saline solution, phial for piercing, frozen at −20° C.

application instructions:
for (a) cocktail in the application for treatment (see (1a)); for application for the diagnosis during the operation 5 to 10 ml of the cocktail are used for producing an infusion solution administered 10 to 30 minutes before the i.v. administration of (b).

Attention has to be paid to the fact that the action of morphine and its derivatives is enhanced by 30 to 40 times as much by the cocktail.

for (b) Jomol fluorescein isothiocyanate is dissolved with 5 ml $H_2O$ (Ampuwa®) and administered intravenously.

For the diagnosis during an operation 10 to 20 minutes after the application of (b) an UV lamp is required (see opthalmology, dentistry).

(10) Jomo-Lab for rapid diagnosis of malignant tumors in vitro constituents: Lyophilisate in laboratory unit degree, not for application in vivo. 300 μg fluorescein isothiocyanate-Jomol, 45 mg NaCl, screw-top bottle, frozen at −20° C.

application instructions: 5 ml $H_2O$ are supplied to the screw-top bottle, the tissue sample is added. The tissue sample is set aside at room temperature for 5 minutes, and then washed in physiological saline solution.

In the cut section of the tissue sample, the tumor tissue is of light color and the healthy tissue is dark when viewed with the magnifying glass or fluorescence microscope in ultraviolet light. The operational preparation margin is also fluorescent due to the proteases released by cell-destroying.

I claim:

1. Jomol derivative pharmaceutical preparation, wherein Jomol is a product obtained from bacteria by a production process in that (a) Nocardia opaca cells (DSM 43 202, ATCC 21953) are cultured on a buffered culture medium, (b) the cells are collected, (c) the cells are suspended in a medium containing glucose and buffer, the suspension is allowed to stand for 15 minutes to several hours, (d) the suspension is treated in a buffer with a murolytic enzyme, and optionally with deoxyribonuclease, (e) the cells are destroyed, (f) the resulting material is separated into sediment and supernatant;

(g) the supernatant is subjected to separation on Sephadex columns using a buffer as eluent, which can optionally contain 0.1 to 0.05% EDTA-Na$_2$, (h) the active fraction is obtained, and (i) the active fraction is reacted with acetaldehyde, and said Jomol derivative is Jomol coupled with a crown ether, diethylene triamine pentaacetic acid, tin-II-chloride, fluorescein isothiocyanate or another dyestuff or a cytostatic.

2. A method for the therapy of malignant tumors and lowered immune defenses comprising the step of administering to a mammal a therapeutically effective amount of the Jomol derivative according to claim 1.

3. Pharmaceutical preparation, characterized in that it contains a Jomol derivative according to claim 1, and a conventional excipient and/or diluent.

4. A method for the therapy of malignant tumors and lowered immune defenses comprising the step of administering to a mammal a therapeutically effective amount of the therapeutic preparation of claim 3.

5. A therapeutic product according to claim 3 characterized in that said Jomol derivative is combined with an adjuvant containing an aldehyde of formula I $$RCHO \qquad (I)$$

wherein R is a hydrogen atom or a straight-chain or branched hydrocarbon group having 1 to 4 carbon atoms, whereby the free aldehyde may also be metabolically liberated directly or indirectly by substances and optionally an alcohol of formula II $$R^1CH_2OH \qquad (II)$$

wherein $R^1$ has the meaning given above for R.

6. The product according to claim 5, characterized in that R and $R^1$ in formulas I and II are a methyl group.

7. A method for the therapy of malignant tumors and lowered immune defenses comprising the step of administering to a mammal a therapeutically effective amount of the therapeutic preparation of claim 5.

8. A method according to claim 7 wherein said Jomol derivative and said adjuvant were administered simultaneously, separately or periodically.

* * * * *